United States Patent [19]

Cussans

[11] Patent Number: 4,965,360

[45] Date of Patent: Oct. 23, 1990

[54] TETRAHYDROISOQUINOLINE COMPOUNDS

[75] Inventor: Nigel J. Cussans, Sandwich, England

[73] Assignee: Pfizer Inc., New York, N.Y.

[21] Appl. No.: 397,605

[22] Filed: Aug. 23, 1989

Related U.S. Application Data

[62] Division of Ser. No. 232,345, Aug. 12, 1988, Pat. No. 4,882,337.

[30] Foreign Application Priority Data

Aug. 15, 1987 [GB] United Kingdom ............... 8719378

[51] Int. Cl.$^5$ ........................................... C07D 217/16
[52] U.S. Cl. ................................. 546/145; 546/144; 546/146; 546/150
[58] Field of Search ........................................ 546/145

[56] References Cited

U.S. PATENT DOCUMENTS

| | | | |
|---|---|---|---|
| 3,855,228 | 12/1974 | Bailey | 544/145 |
| 4,656,174 | 4/1987 | Campbell et al. | 514/254 |
| 4,686,228 | 8/1987 | Campbell et al. | 514/307 |
| 4,758,568 | 7/1988 | Campbell et al. | 514/254 |

FOREIGN PATENT DOCUMENTS 0100200 2/1984 European Pat. Off. .

OTHER PUBLICATIONS

Campbell, et al., "Chemical Abstracts", vol. 101, 1984, col. 101:7051e.
Campbell, et al., "Chemical Abstracts", vol. 102, 1985, col. 105:45882e.

*Primary Examiner*—Glennon H. Hollrah
*Assistant Examiner*—James H. Turnipseed
*Attorney, Agent, or Firm*—Peter C. Richardson; Paul H. Ginsburg

[57] ABSTRACT

Novel 4-amino-6,7-dimethoxy-2-(6,7-disubstituted-1,2,3,4-tetrahydroisoquinol-2-yl)quinoline compounds have been prepared, including their pharmaceutically acceptable salts and various novel key intermediates therefor. These compounds are useful in therapy as anti-arrhythmic agents and therefore, are of value in the treatment of various cardiac arrhythmias. Preferred compounds include 4-amino-6,7-dimethoxy-2-(6-hydroxy-7-methoxy-1,2,3,4-tetrahydroisoquinol-2-yl)quinoline and 4-amino-6,7-dimethoxy-2-(7-hydroxy-6-methoxy-1,2,3,4-tetrahydroisoquinol-2-yl)-quinoline. Methods for preparing these compounds from known starting materials are provided.

3 Claims, No Drawings

TETRAHYDROISOQUINOLINE COMPOUNDS

This is a division, of application Ser. No. 07/232,345, filed on Aug. 12, 1988 now U.S. Pat. No. 4,882,337.

BACKGROUND OF THE INVENTION

This invention relates to certain 4-amino-6,7-dimethoxy-2-(6,7-disubstituted-1,2,3,4-tetrahydroisoquinol-2-yl)quinolines which are useful in the treatment of cardiac arrhythmias in human subjects.

SUMMARY OF THE INVENTION

Thus the invention provides compounds of the formula:

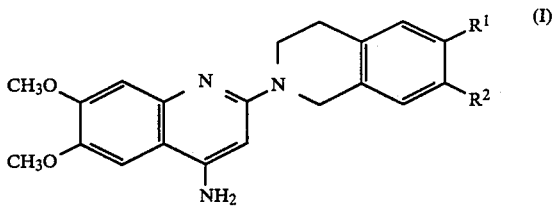

and their pharmaceutically acceptable salts, wherein one of $R^1$ and $R^2$ is methoxy and the other is a group of the formula —OH, —O.CO($C_1$–$C_4$ alkyl), —O.COPh or —O.COCH$_2$Ph where Ph is a phenyl group optionally substituted by one or two substituents each independently selected from F, Cl, Br, I, $CF_3$, $C_1$–$C_4$ alkyl and $C_1$–$C_4$ alkoxy.

Preferably, either $R^1$ is hydroxy and $R^2$ is methoxy or $R^1$ is methoxy and $R^2$ is hydroxy.

DETAILED DESCRIPTION OF THE INVENTION

The compounds of the formula (I) in which one of $R^1$ and $R^2$ is methoxy and the other is hydroxy can be prepared by the cyclisation of a compound of the formula:

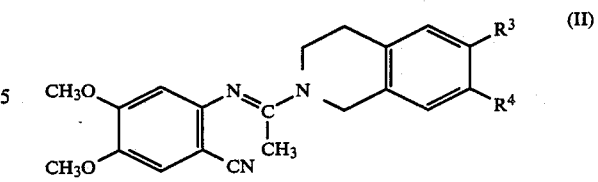

wherein one of $R^3$ and $R^4$ is methoxy and the other is either hydroxy or a protected hydroxy group, preferably benzyloxy. It is preferred to use a protected hydroxy group.

The intermediates of the formula (II) also form a part of the invention.

The cyclisation is preferably carried out with a Lewis acid, e.g. zinc chloride or bromide, or aluminum chloride. The use of zinc chloride is preferred. The reaction is typically carried out by heating the compound (II) with zinc chloride in a suitable organic solvent, e.g. dimethylacetamide, and preferably under reflux. The reaction mixture is then treated with a base such as aqueous 2.0–2.5N sodium hydroxide to destroy any complexes that the zinc chloride may form with the end product. The product can then be isolated and purified by conventional techniques.

When one of $R^3$ and $R^4$ is protected hydroxy group, then the protecting group will need to be removed after cyclisation to generate compounds of formula (I) where $R^1$ or $R^2$ is OH. Benzyl groups are typically removed by hydrogenating the benzyloxy compound in methanol at about $2.068 \times 10^5$ Pa (30 psi) at room temperature in the presence of a palladium-on-carbon catalyst.

The compounds of the formula (I) in which one of $R^1$ and $R^2$ is —O.CO($C_1$–$C_4$ alkyl), —O.COPh or —O.COCH$_2$Ph can be prepared by the acylation of the corresponding hydroxy-compounds according to conventional techniques, e.g. using an appropriate acid chloride or anhydride. Protection of the 4-amino group is not usually necessary.

The intermediates of the formula (II) in which $R^3$ is methoxy and $R^4$ is benzyloxy can be prepared as follows:

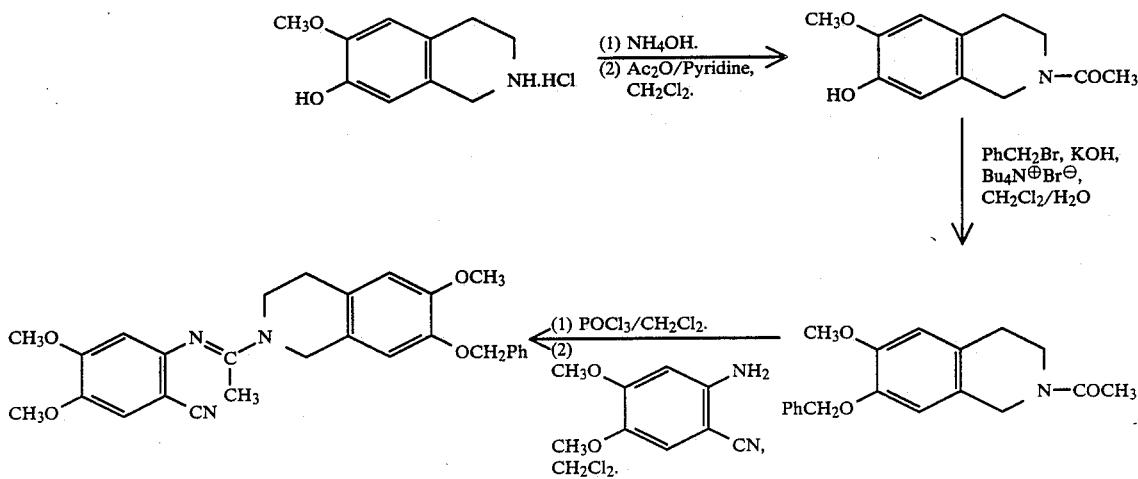

Similarly, the intermediates of the formula (II) in which $R^3$ is benzyloxy and $R^4$ is methoxy can be prepared from the corresponding 6-hydroxy-7-methoxytetrahydroisoquinoline.

The intermediates of the formula (II) in which one of $R^3$ and $R^4$ is methoxy and the other is hydroxy can be prepared similarly to the above but with the omission of the benzylation step and provided that the level of phosphorus oxychloride is increased in the final step.

The 1,2,3,4-tetrahydroisoquinoline hydrochloride starting materials are described in J. Org. Chem., vol. 30, pages 2247-2250 (July 1965).

Also according to the invention, there is provided a method of treatment of cardiac arrhythmias which comprises administering to a human subject suffering from or liable to cardiac arrhythmias an effective cardiac arrhythmia reducing or preventing amount of a compound of formula (I) or a pharmaceutically acceptable salt thereof.

The invention also provides a compound of the formula (I), or a pharmaceutically acceptable salt thereof, for use as a medicament.

Also, the invention further provides the use of the compound of formula (I), or of a pharmaceutically acceptable salt thereof, for the manufacture of a medicament for the prevention or reduction of cardiac arrhythmias.

The ability of the compounds of the formula (I) to reduce or prevent cardiac arrhythmias can be assessed by their antagonism of adrenaline-induced ventricular arrhythmias when administered intravenously to anaesthetised dogs.

The ability of the compounds of the formula (I) to reduce or prevent cardiac arrhythmias can also be assessed by their ability to antagonise pictrotoxin-induced ventricular arrhythmias in anaesthetised cats.

It is expected that for human use in the prevention or reduction of cardiac arrhythmias single, oral dosages of a compound of formula (I) will be in the range from 0.1 to 10.0 mg per day for an average adult patient (70 kg), taken in up to 4 doses per day. Thus individual tablets or capsules might contain from 0.025 to 10.0 mg of active compound, in a suitable pharmaceutically acceptable vehicle or carrier. Single dosages for parenteral, e.g. intravenous, administration would be expected to be within the range from 0.1 to 10 micrograms/kg taken in up to 4 doses per day, e.g. 5 to 1000 micrograms, as required. A severe cardiac arrhythmia is preferably treated by the intravenous route, in order to effect a rapid conversion to normal sinus rhythm. Variations on these dosages may occur depending on the weight and condition of the subject being treated, as will be determined by the medical practitioner.

The compounds of the formula (I) and their pharmaceutically acceptable salts can be administered alone, but will generally be administered in admixture with a pharmaceutical carrier selected with regard to the intended route of administration and standard pharmaceutical practice. They can be administered both to patients suffering from arrhythmias and also prophylactically to those likely to develop arrhythmias. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic with blood.

The pharmaceutically acceptable acid addition salts of the compound of the formula (I) are salts formed from acids which form non-toxic salts such as the hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, benzenesulphonate and p-toluenesulphonate salts. Since the compounds of the formula (I) are phenolic, they may also form metal salts, e.g. alkali metal salts such as sodium salts.

The antiarrhythmic properties of the compounds of formula (I) may also be enhanced by use in combination with a non-selective beta-adrenoceptor blocking compound, such as propranolol, or with a cardio-selective beta-adrenoceptor blocking agent, such as atenolol.

The following Examples, in which all temperatures are in ° C., illustrate the invention. "Merck Art.9385" is the trade mark of a brand of silica.

EXAMPLE 1

4-Amino-6,7-dimethoxy-2-(6-hydroxy-7-methoxy-1,2,3,4-tetrahydroisoquinol-2-yl)quinoline

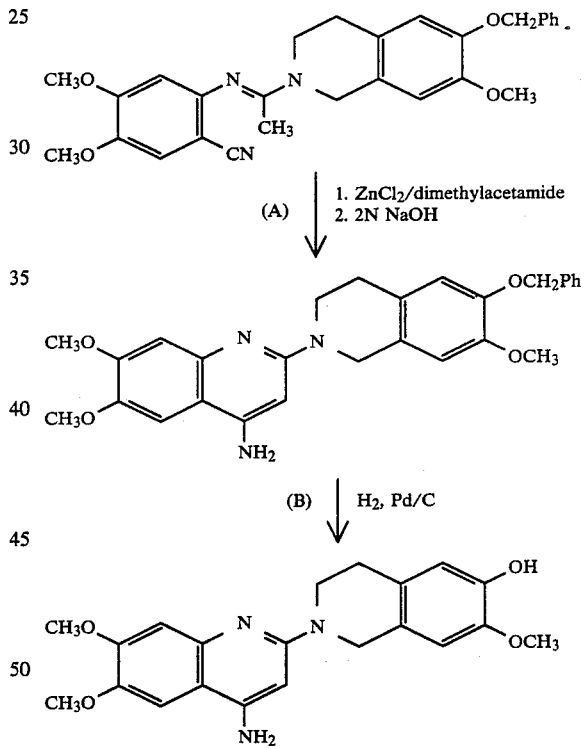

(A)
4-Amino-2-(6-benzyloxy-7-methoxy-1,2,3,4-tetrahydroisoquinol-2-yl)-6,7-dimethoxyquinoline N-(1-[6-benzyloxy-7-methoxy-1,2,3,4-tetrahydroisoquinol-2-yl]ethylidene)-2-cyano-4,5-dimethoxyaniline (10.92 g), anhydrous zinc chloride (3.16 g) and dimethylacetamide (25 ml) were mixed at 20° and then stirred at reflux for two hours. The reaction mixture was allowed to cool to about 40° and then 2N sodium hydroxide (16 ml) was added. The mixture was cooled to 25° and stirred for fifteen minutes. 2N Sodium hydroxide (10 ml) and water (50 ml) were added and the reaction mixture was then extracted with methylene chloride (3×100 ml). The combined organic extracts were washed (H₂O), dried (MgSO₄) and evaporated in vacuo. The residue was chromatographed on silica (Merck "ART.9385") under medium pressure eluting with methylene chloride containing gradually increasing amounts (1–20%) of methanol. The combined product-containing fractions were evaporated and the residue was recrystallised from ethanol and washed (Et₂O) to give 4-amino-2-(6-benzyloxy-7-methoxy-1,2,3,4-tetrahydroisoquinol-2-yl)-6,7-dimethoxyquinoline (7.1 g) as a pale yellow powder, m.p. 181°–2°.

Analysis %:-
Found: C,70.81; H,6.50; N,8.68;
Calculated for C₂₈H₂₉N₃O₄: C,71.32; H,6.20; N,8.91.

(B) 4-Amino-6,7-dimethoxy-2-(6-hydroxy-7-methoxy-1,2,3,4-tetrahydroisoquinol-2-yl)quinoline A suspension of the product of part (A) (3.0 g) in methanol (400 ml) was warmed at about 50° until the majority of the product dissolved. The reaction mixture was then transferred to a hydrogenator and hydrogenated under a hydrogen pressure of 2.068×10⁵ Pa (30 psi) in the presence of 5% Pd/C (400 mg) at room temperature with stirring for 1.5 hours. The reaction mixture was filtered through "Arbacel" (a microcrystalline cellulose filtration aid), and evaporated to yield impure 4-amino-6,7-dimethoxy-2-(6-hydroxy-7-methoxy-1,2,3,4-tetrahydroisoquinol-2-yl)quinoline (600 mg). The catalyst was then stirred in methylene chloride/methanol (4:1, 200 ml) for 30 minutes, and the mixture was filtered and the filtrate evaporated to yield a further 1.05 g of the impure product. The total of the impure product (1.65 g) was dissolved in methylene chloride/methanol (4:1, 300 ml) and shaken with 10% sodium carbonate solution (50 ml). The organic phase was washed (H₂O), dried and evaporated. Medium pressure chromatography of the residue on silica (Merck "Art.9385") eluting with methylene chloride containing gradually increasing amounts of ethanol (1–25%) followed by collection and evaporation of appropriate fractions gave the title compound. The compound was slurried in boiling methylene chloride (20 ml), cooled, precipitated with hexane, filtered, and the solid washed with hexane and dried to give the pure title compound as a quarter-hydrate (900 mg), m.p. 250°–251°.

Analysis %:
Found: C,65.62; H,6.27; N,10.47;
Calculated for C₂₁H₂₃N₃O₄.1/4 H₂O: C,65.35; H,6.14; N,10.89.

EXAMPLE 2

4-Amino-6,7-dimethoxy-2-(7-hydroxy-6-methoxy-1,2,3,4-tetrahydroisoquinol-2-yl)quinoline (A) 4-Amino-2-(7-benzyloxy-6-methoxy-1,2,3,4-tetrahydroisoquinol-2-yl)-6,7-dimethoxyquinoline, m.p. 198°–9°, was prepared similarly to Example 1(A), using the product of Preparation 6, zinc chloride, dimethylacetamide, and 2.5N NaOH.

Analysis %:
Found: C,70.24; H,6.02; N,8.79;
Calculated for C₂₈H₂₉N₃O₄.½H₂O: C,69.98; H,6.29; N,8.74.

(B) 4-Amino-6,7-dimethoxy-2-(7-hydroxy-6-methoxy-1,2,3,4-tetrahydroisoquinol-2-yl)quinoline hydrochloride, m.p. 204°–5°, was prepared similarly to Example 1(B) by the reduction of the corresponding 7-benzyloxy compound with H₂/Pd/C in methanol. In this instance the product was isolated as a hydrochloride. This is believed to be due to the presence of chloride ions in the catalyst.

Analysis %:
Found: C.60.18; H,5.75; N,9.55;
Calculated for C₂₁H₂₃N₃O₄.HCl: C,60.35; H,5.79; N,10.06.

The following Preparations, in which all temperatures are in ° C., illustrate the preparation of certain starting materials:

Preparation 1

N-Acetyl-6-hydroxy-7-methoxy-1,2,3,4-tetrahydroisoquinoline

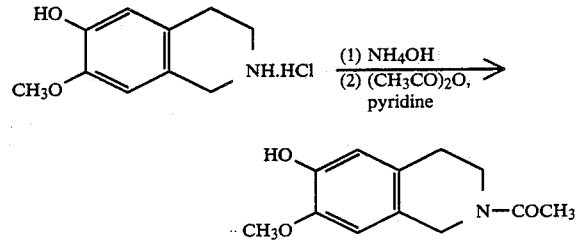

6-Hydroxy-7-methoxy-1,2,3,4-tetrahydroisoquinoline hydrochloride (15.47 g) was converted to the free base by dissolving it in water (about 100 ml) and adding concentrated (0.88) aqueous ammonia to pH 9–10, giving a precipitate of the free base. The precipitate refused to extract completely into chloroform (100 ml.). The aqueous phase was therefore filtered and the solid washed (EtOH) and dried. The chloroform extract was dried (MgSO₄) and evaporated. The two solids were combined to give the free base as a pale powder (11.94 g).

A suspension of the free base (11.94 g) in methylene chloride (400 ml) was stirred at 10°, pyridine (5.66 ml) was added followed by the slow dropwise addition of acetic anhydride (6.6 ml) in methylene chloride (10 ml). Solution soon resulted and the reaction mixture was then stirred for two hours whilst allowing the temperature to rise slowly to room temperature. The reaction mixture was washed with water (100 ml), 2N HCl (100 ml) and then water again (100 ml), dried (MgSO₄) and evaporated to give the title compound as a quarter-hydrate, (14.03 g), m.p. 139°–140°.

Analysis %:
Found: C,63.51; H,6.69; N,6.07;
Calculated for C₁₂H₁₅NO₃.1/4 H₂O: C,63.84; H,6.92; N,6.21.

The tetrahydroisoquinoline hydrochloride starting material is described in J. Org. Chem., vol. 30, July 1965, pages 2247–2250. An alternative preparation of the title compound is described in J. Org. Chem., Vol. 36, no. 20, 1971, pages 3006–3010.

Preparation 2

N-Acetyl-7-hydroxy-6-methoxy-1,2,3,4-tetrahydroisoquinoline

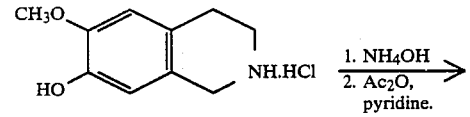

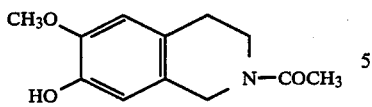

7-Hydroxy-6-methoxy-1,2,3,4-tetrahydroisoquinoline hydrochloride (2.60 g) was dissolved in water and the solution was basified to pH 9 with concentrated (0.88) aqueous ammonia. The free base was extracted with methylene chloride/ethanol (9:1) (3×200 ml). The organic extracts were combined, washed (H₂O), dried (MgSO₄) and evaporated to dryness. The residue was azeotroped with methylene chloride, evaporated, and the residue was suspended in methylene chloride (100 ml). Pyridine (1.05 ml) was added dropwise at 10° followed by acetic anhydride (1.25 ml) and the resulting mixture was allowed to stand over a weekend (about 68 hours). The solution was washed with 2N HCl, then with water, dried (MgSO₄) and evaporated. Medium pressure chromatography on silica (Merck "Art.9385") eluting with methylene chloride containing gradually increasing amounts of methanol (0–3%) followed by collection and evaporation of appropriate fractions gave the title compound as a quarter-hydrate (1.05 g), m.p. 142°–144°.

Analysis %:
Found: C,63.49; H,6.50; N,5.96;
Calculated for $C_{12}H_{15}NO_3 \cdot 1/4\ H_2O$: C,63.84; H,6.92; N,6.21.

The tetrahydroisoquinoline hydrochloride starting material is described in J. Org. Chem., vol. 30, July 1965, pages 2247–2250. An alternative preparation of the title compound is described in J. Org. Chem., vol. 36, no. 20, 1971, pages 3006–3010.

Preparation 3

N-Acetyl-6-benzyloxy-7-methoxy-1,2,3,4-tetrahydroisoquinoline

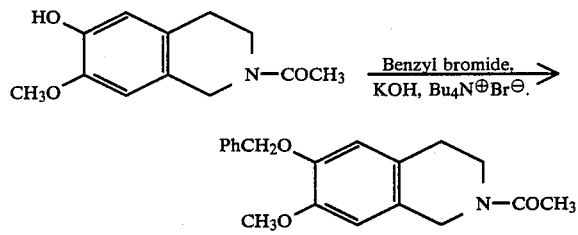

N-Acetyl-6-hydroxy-7-methoxy-1,2,3,4-tetrahydroisoquinoline quarter-hydrate (14.0 g) was dissolved in methylene chloride (200 ml). Benzyl bromide (22.6 ml) was then added, followed by the addition of a solution of potassium hydroxide (4.62 g) in water (200 ml) and then tetra-n-butylammonium bromide (2.04 g). The resulting mixture was stirred vigorously overnight (16 hours). The organic layer was then separated, washed (H₂O), dried (MgSO₄) and evaporated. Medium pressure chromatography of the residue on silica (Merck "Art.9385") eluting with methylene chloride containing gradually increasing amounts of methanol (0–10%) gave, after collection and evaporation of appropriate fractions, the title compound as a semi-solid which was recrystallised from ethyl acetate to give the pure title compound, 16.84 g, m.p. 125°–6°.

Analysis %:
Found: C,73.05; H,6.56; N,4.42;
Calculated for $C_{19}H_{21}NO_3$: C,73.29; H,6.80; N,4.50.

Preparation 4

N-Acetyl-7-benzyloxy-6-methoxy-1,2,3,4-tetrahydroisoquinoline, m.p. 105°, was prepared similarly to the previous Preparation, starting from the corresponding 7-hydroxy-1,2,3,4-tetrahydroisoquinoline, benzyl bromide, aqueous potassium hydroxide and tetrabutylammonium bromide.

Analysis %:
Found: C,72.02; H,6.89; N,4.29;
Calculated for $C_{19}H_{21}NO_3 \cdot 1/4\ H_2O$: C,72.24; H,6.86; N,4.43.

Preparation 5

N-(1-[6-Benzyloxy-7-methoxy-1,2,3,4-tetrahydroisoquinol-2-yl]ethylidene)-2-cyano-4,5-dimethoxyaniline

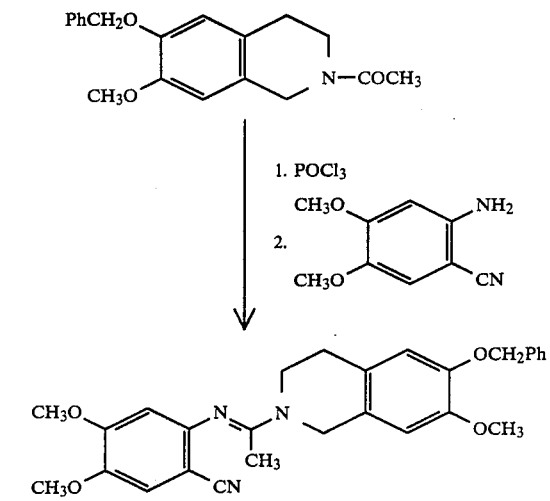

The free base of 2-cyano-4,5-dimethoxyaniline (see J. Amer. Chem. Soc., 68, page 1903 [1946]) was prepared by dissolving the hydrochloride in saturated aqueous sodium bicarbonate solution to pH 8, extracting with methylene chloride, washing the organic extract with water, drying (MgSO₄) and evaporating. Medium pressure chromatography of the residue on silica (Merck "MK.9385") eluting with methylene chloride followed by collection and evaporation of appropriate fractions gave the pure free base.

Phosphorus oxychloride (3.24 ml) was added over 1 minute to a stirred solution of N-acetyl-6-benzyloxy-7-methoxy-1,2,3,4-tetrahydroisoquinoline (10 g) in methylene chloride (100 ml) at 10°. After stirring for twenty minutes at room temperature, a solution of 2-cyano-4,5-dimethoxyaniline (5.72 g) in methylene chloride (80 ml) was added and the resulting suspension was heated at reflux for 16 hours. The reaction mixture was then allowed to cool, water (60 ml) was added followed by 40% sodium hydroxide to pH 8–9 with stirring for five minutes. The organic layer was then separated and the aqueous phase extracted with methylene chloride (3×50 ml). The combined organic layers were washed (H₂O), dried (MgSO₄) and evaporated. The residue was chromatographed on silica (Merck Art.9385) under medium pressure, eluting with methylene chloride containing gradually increasing amounts of methanol (0–10%). Some impure product-containing fractions were re-chromatographed on silica but using methylene chloride containing 2–4% methanol. The pure product-containing fractions were combined, evaporated, and the residue recrystallised from ethyl acetate to give the title compound as a colourless powder (11.02 g), m.p. 164°–5° (d).

Analysis %:
Found: C,71.46; H,6.18; N,9.15;
Calculated for $C_{28}H_{29}N_3O_4$: C,71.32; H,6.20; N,8.91.

Preparation 6

N-(1-[7-Benzyloxy-6-methoxy-1,2,3,4-tetrahydroisoquinol-2-yl]ethylidene)-2-cyano-4,5-dimethoxyaniline The title compound, m.p. 72°–3°, was prepared similarly to the procedure of the previous Preparation, starting from N-acetyl-7-benzyloxy-6-methoxy-1,2,3,4-tetrahydroisoquinoline, phosphorus oxychloride, and 2-cyano-4,5-dimethoxyaniline.

Analysis %:
Found: C,71.04; H,6.16; N,8.64;
Calculated for $C_{28}H_{29}N_3O_4$: C,71.32; H,6.20; N,8.91.

I claim:
1. A compound of the formula:

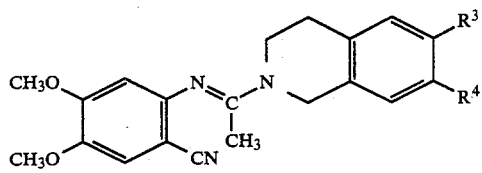

wherein one of $R^3$ and $R^4$ is methoxy and the other of $R^3$ and $R^4$ is hydroxy or benzyloxy.

2. A compound as claimed in claim 1 wherein $R^3$ is methoxy and $R^4$ is benzyloxy.

3. A compound as claimed in claim 1 wherein $R^3$ is benzyloxy and $R^4$ is methoxy.

* * * * *